United States Patent [19]

Planker et al.

[11] 4,217,307
[45] Aug. 12, 1980

[54] PROCESS FOR THE PREPARATION OF 2,2'-DICHLORO-HYDRAZOBENZENE

[75] Inventors: Siegfried Planker, Königstein; Konrad Baessler; Otto Fuchs, both of Frankfurt am Main, all of Fed. Rep. of Germany

[73] Assignee: Hoechst Aktiengesellschaft, Fed. Rep. of Germany

[21] Appl. No.: 927,856

[22] Filed: Jul. 25, 1978

[30] Foreign Application Priority Data

Jul. 27, 1977 [DE] Fed. Rep. of Germany ....... 2733747

[51] Int. Cl.$^2$ .......................................... C07C 109/04
[52] U.S. Cl. ..................................... 260/569; 260/578
[58] Field of Search ........................................ 260/569

[56] References Cited

U.S. PATENT DOCUMENTS

| | | | |
|---|---|---|---|
| 3,156,724 | 11/1964 | Werner et al. | 260/569 |
| 3,527,805 | 9/1970 | Pregazlia et al. | 260/569 |

Primary Examiner—Robert V. Hines
Attorney, Agent, or Firm—Connolly and Hutz

[57] ABSTRACT

The catalytic hydrogenation of o-nitro-chlorobenzene in aqueous alkali metal hydroxide solution with addition of an aromatic non-watermiscible solvent at an elevated temperature and under pressure using a noble metal catalyst and a polycyclic quinone as a co-catalyst leads to high and well-reproducible yields of 2,2'-dichloro-hydrazobenzene when the quinone is a derivative of anthraquinone, especially a hydroxy-anthraquinone. The product is obtained in so high a quality that it can be transformed without isolation or purification into 3,3'-dichlorobenzidine.

20 Claims, No Drawings

PROCESS FOR THE PREPARATION OF 2,2'-DICHLORO-HYDRAZOBENZENE

The present invention relates to the preparation of 2,2'-dichloro-hydrazobenzene.

The invention provides a process for the preparation of 2,2'-dichloro-hydrazobenzene by catalytic reduction of o-nitro-chlorobenzene with hydrogen.

It is known from U.S. Pat. No. 3,156,724 to prepare 2,2'-dichloro-hydrazobenzene by catalytic hydrogenation of o-nitro-chlorobenzene. The hydrogenation catalyst consists of palladium or platinum. As reaction medium there is used a 2 to 20% aqueous solution of sodium or potassium hydroxide, especially a 13 to 14% sodium hydroxide solution, optionally while adding an organic solvent, preferably a non-water-miscible aromatic hydrocarbon, such as benzene, toluene or xylene. The temperature is in the range of from 40° to 100° C., preferably from 60° to 70° C., the hydrogen (over-)pressure is in the range of from about 0.4 to 7.8 bars (20 to 125 psi, abs.), preferably from about 0.75 to 1.8 bars (25 to 40 psi, abs.). For the formation of 2,2'-dichloro-hydrazobenzene, additives of naphthalene derivatives, such as naphthoquinone-(1,4) or 2,3-dichloro-naphthoquinone-(1,4) are added to the reaction mixture. The yields of 2,2'-dichloro-hydrazobenzene thus obtained vary between 80 and 90%, the splitting-off of chlorine is stated to be insignificant.

As was found in a reaction carried out accordingly, a repeated use of the noble metal catalysts not only leads to yields getting smaller with every successive batch, but at the same time the reaction times are increasing with a declining activity of the noble metal catalysts. Both results are undesired for an economical performance of the reduction. The splitting-off of chlorine of from 7 to 8% is high already in the first run.

Surprisingly, it has now been found that the catalytic reduction of o-nitro-chlorobenzene to give 2,2'-dichloro-hydrazobenzene with hydrogen in an aqueous sodium or potassium hydroxide solution, especially a 10 to 25% by weight sodium hydroxide solution, and in the presence of a non-water-miscible aromatic solvent, especially a hydrocarbon, such as benzene, toluene or xylene, with noble metal catalysts, preferably palladium, platinum or modified, for example sulfided (according to U.S. Pat. Nos. 3,761,425 and 3,920,743), especially sulfided platinum-on-carbon catalysts (according to U.S. Pat. Nos. 3,803,054 and 3,929,891), at a hydrogen (over-)pressure of from 1 to about 10, preferably up to 6 bars and a reduction temperature of from about 50° to 80°, especially 60° C., leads to high and well reproducible yields, if as a co-catalyst there is added a derivative of anthraquinone, preferably a hydroxy-anthraquinone, for example β-hydroxy-anthraquinone or 2,6-dihydroxy-anthraquinone.

It is a special advantage that with the use of the anthraquinone derivatives the noble metal catalysts may be recycled many times without suffering a reduction in activity. Even after using the noble metal catalysts ten times, for example, constant yields are obtained in the same reduction period as in the starting batch.

The anthraquinone derivatives accelerate the reduction of the individual reaction stages, especially the azoxy and azo stages, to a considerably higher degree than the naphthoquinone compounds, so that a lower temperature is possible during the entire reaction period, and even shorter reaction times are obtained than when using the known naphthoquinones.

In addition, the splitting-off of chlorine has been strongly reduced: it is 4% with the use of palladium, less than 2% with unmodified platinum and less than 1% with sulfited platinum (prepared according to U.S. Pat. Nos. 3,803,054 and 3,929,891). It was surprising that the sulfited platinum catalyst which so far has appeared to be suitable only for the catalytic reduction of halogen-containing nitroaromatic compounds to give the corresponding amines in the neutral or slightly acid medium may also be used for the reduction of o-nitrochlorobenzene to give 2,2'-dichloro-hydrazobenzene in a strongly alkaline solution.

It is another advantage that for example the β-hydroxyanthraquinone can be precipitated practically quantitatively from the aqueous mother liquor after the reduction by adjusting the pH value of 3 to 4 and can be used again several times without purification, whereas the 2-hydroxy-3-chloronaphthoquinone-(1,4) (formed in the course of the reduction from 2,3-dichloro-naphthoquinone-(1,4)) must be eliminated by a complicated purification of the waste water.

The amount of anthraquinones used is small; it is less than that of the naphthoquinone derivatives. Thus, for example, a weight ratio of β-hydroxy-anthraquinone to o-chloronitrobenzene of 0.003 to 0.008, especially of 0.004:1, is sufficient also to complete uniformly the reduction of the dichloroazoxybenzene occurring as intermediate stage via the dichloroazobenzene to reach the hydrazo compound, whereas twice the amount of 2,3-dichloronaphthoquinone-(1,4) is required in order to obtain at least comparable results in the first application of the noble metal catalysts.

It is of importance for the economy of the process that the noble metal catalyst is only to be used—with a reliable reproducibility of the yields and product properties also after repeated use—in a weight ratio of the nitro compound to platinum or palladium of from about 4000:1 to 1500:1, preferably 2500:1.

As reaction medium there is used a 16 to 25% sodium hydroxide solution in an amount that after the completion of the reaction a 10 to 15% sodium hydroxide solution is obtained due to the resulting reaction water.

In this case, too, the anthraquinones offer advantages as compared with the naphthoquinones. While with naphthoquinones the best results are obtained with a 16% sodium hydroxide solution in a weight ratio of o-nitrochlorobenzene to NaOH (100%) of 1:0.095, the anthraquinones permit an increase of the NaOH concentration of up to 25% and a smaller amount of sodium hydroxide solution in a weight ratio of o-nitrochlorobenzene to NaOH (100%) of 1:0.071, without slowing down the reaction rate. The use of an approximately 25% NaOH as compared with a 16% NaOH means in the above-indicated weight ratios an increase of the space yield of about 20%.

The reaction temperature is preferably between 55° and 60° C., and the hydrogen pressure is preferably between 1 and 6 bars, in which process it is advantageous to slowly increase the pressure during the reduction within the indicated limits.

In the process of the invention the reduction of o-nitrochlorobenzene to 2,2'-dichloro-hydrazobenzene is carried out while using a non-water-miscible solvent, such as benzene, toluene, xylene, ethylbenzene or the technical mixtures thereof, for example the mixture of m-xylene and ethylbenzene which is known in commerce by the name of "Solventnaphtha".

The reduction is effected in a particularly advantageous manner by introducing o-nitrochlorobenzene, aqueous sodium hydroxide solution, the anthraquinone derivative, for example β-hydroxy-anthraquinone, the solvent, an emulsifying agent and a noble metal catalyst into a conventional autoclave and heating the mixture, while stirring, after having displaced the air by nitrogen. The nitrogen is replaced by hydrogen, which is pressed on the mixture until a decrease of pressure is no longer observed. The desired reaction temperature is maintained by cooling or heating from the outside.

Upon completion of the reduction the catalyst is filtered off under a nitrogen atmosphere and is recycled into the next reduction charge, in which process it may be used at least ten times.

In order to determine the yield, after separating the aqueous phase from the solvent phase in which the 2,2'-dichloro-hydrazobenzene formed and o-chloroaniline are dissolved, the o-chloroaniline is washed out with diluted hydrochloric acid, the solvent is distilled off and the hydrazo compound is dried. Since the product is obtained in sufficient purity, the organic phase may also be subjected directly to the rearrangement with mineral acids to give 3,3'-dichlorobenzidine.

The process of the invention thus permits to prepare 2,2'-dichloro-hydrazobenzene in a particularly economical manner by the catalytic reduction of o-nitrochlorobenzene in the presence of anthraquinones in high and well reproducible yields. The advantages of the process according to the invention may be further illustrated by way of the following Examples. The percentages are by weight, unless otherwise stated.

EXAMPLE 1

The following chemicals are introduced into a 2 liter steel autoclave with a magnetically agitated stirrer, a heating device and a cooler;
630 g of o-nitro-chlorobenzene (4 moles),
200 ml of "Solventnaphtha",
180 g of 25% sodium hydroxide solution,
2.5 g of β-hydroxy-anthraquinone,
2 g of emulsifying agent (commercial emulsifying mixture, consisting essentially of sodium dodecylbenzene sulfonate with small portions of oleic acid, the sodium salt of a $C_{13}$-$C_{15}$-alkyl-sulfamidocarboxylic acid and slightly chlorinated long-chain hydrocarbons in aqueous iso-butanol),
0.25 g of palladium in the form of 5 g of 5% palladium-on-carbon catalyst.

After displacing the air in the closed autoclave by nitrogen, the reaction mixture is heated, while stirring, to 60° C., and hydrogen is pressed in up to 3 bars. In accordance with the hydrogen absorption, the hydrogen pressure is increased to 6 bars up to the completion of the reduction. The reduction is completed when the absorption of hydrogen is discontinued, which is the case after 5 hours. Upon completion of the reaction the reaction mixture is heated to 80° C., and at this temperature the palladium-on-carbon catalyst is filtered off. The filtrate is diluted with 600 ml of "Solventnaphtha" and the organic phase containing the 2,2'-dichloro-hydrazobenzene as well as the o-chloroaniline formed as by-product is separated from the aqueous phase.

In order to determine the yield, the o-chloroaniline is extracted in common manner by washing twice with 5% hydrochloric acid, and the "Solventnaphtha" is eliminated in vacuo.

The yield is 84% of the theory of 2,2'-dichlorohydrazobenzene having a melting point of from 85° to 86° C. as well as 10% of the theory of o-chloroaniline, each calculated on the o-nitrochlorobenzene used.

The palladium-on-carbon catalyst filtered off is again used at least 10 times without purification, and the reduction is carried out in the same manner. In all subsequent batches the same amount of 2,2'-dichlorohydrazobenzene as in the starting batch is obtained without any reduction in quality. The reduction period is about 5 hours constantly.

The determination of the splitting-off of chlorine is effected in the aqueous phase by potentiometric titration and is in all batches 4% each at a maximum, calculated on o-nitrochlorobenzene.

COMPARISON EXAMPLE ad 1

Example 1 is repeated, however, 5 g of 2,3-dichloronaphthoquinone-(1,4) are used instead of the hydroxy-anthraquinone. Upon reaching the azoxy stage, the reaction stops at a reaction temperature of 60° C. and can only be completed by increasing the reaction temperature to 80° C. The yield is 80% of the theory, calculated on o-nitrochlorobenzene. The reduction takes 6.25 hours.

Upon re-using the palladium catalyst, the yield decreases uniformly and is only 76% of the theory, for example, after recycling the catalyst 4 times, whereas the reduction period rises to 8 hours. The splitting-off of chlorine is 8%, calculated on o-nitrochlorobenzene.

EXAMPLE 2

In accordance with Example 1 the reaction is carried out using
630 g of o-nitrochlorobenzene,
200 ml of toluene,
180 g of 25% NaOH,
2.5 g of 2,6-dihydroxy-anthraquinone,
2 g of emulsifying agent (as in Example 1) and
0.25 g of platinum in the form of 5 g of 5% platinum-on-carbon catalyst.

The yield is 83% of the theory of 2,2'-dichlorohydrazobenzene, calculated on o-nitrochlorobenzene, with a melting point of from 84° to 86° C., the reaction period being 5 hours. After recycling the platinum catalyst 10 times, the yields and the reaction times are constant. The splitting-off of chlorine is 1.7% of the theory at a maximum, calculated on o-nitrochlorobenzene.

EXAMPLE 3

The process is carried out as has been described in Example 1, however, while using instead of the palladium catalyst 0.25 g of platinum in the form of 10 g of sulfited 5% platinum-on-carbon catalyst having a water content of 50% (corresponding to U.S. Pat. Nos. 3,803,054 and 3,929,891). The yield is 83% of theory of 2,2'-dichloro-hydrazobenzene, calculated on o-nitrochlorobenzene, with a melting point of from 85° to 86° C., the reaction period being 5 hours. After recycling the platinum catalyst 10 times, the yields and reaction times were constant. The splitting-off of chlorine is 0.7% of the theory at a maximum, calculated on o-nitrochlorobenzene.

APPENDIX: Preparation of sulfided and sulfited platinum-on-carbon catalysts (A) Sulfided platinum-on-carbon catalyst according to Example 1 of U.S. Pat. Nos. 3,761,425 and 3,920,743

EXAMPLE 1

In a high energy stirring device supplied with nitrogen, 25 g of a catalyst of the type of 5% platinum-on-carbon (crystallite size: about 10 Angstrom units; metal surface area: about 10 m$^2$/g; specific surface area (BET): 800 m$^2$/g; size of the carbon particles: about 44%<20μ; about 99%<80μ) were carefully suspended in a mixture of 500 ml of water and 8 g of 75% sulfuric acid at a temperature of 22° C. The solids were allowed to deposit, and the nitrogen covering the liquid was expelled by hydrogen. Into the closed apparatus, hydrogen was passed into the well-stirred suspension, from a storage cylinder having a liquid jacket regulated by a thermostat. About 30 minutes later, the saturation was complete. The volume of the occluded hydrogen could be checked from a scale of the storage cylinder. It amounted to 600–630 ml at 22° C. Then the hydrogen covering the sedimentary catalyst was substituted by hydrogen sulfide gas. The gassing with H$_2$S was effected while stirring in a similar way as the gassing carried through with H$_2$ from a graduated cylinder controlled by a thermostat, the apparatus being closed. When about 300 ml of H$_2$S were absorbed at 22° C., stirring was stopped, and the apparatus was flushed with nitrogen until it was free from hydrogen sulfide. The catalyst was separated from the liquid by filtration and washed with distilled water. It was applied in moist state with a water content of about 50%.

(B) Sulfited platinum-on-carbon catalyst according to Example 1 of U.S. Pat. Nos. 3,803,054 and 3,929,891

EXAMPLE 1

In a flask provided with stirrer and filled with nitrogen, 25 g of a catalyst of the 5%-platinum-on-carbon type (active surface area: about 800 m$^2$/g, crystallite size: about 10 Angstrom units, metal surface: about 10 m$^2$/g) were carefully suspended in 500 cc of a 1 percent aqueous sulfuric acid at a temperature of 25° C. The suspension was allowed to deposit and the nitrogen covering the liquid was expelled by means of hydrogen. Hydrogen was then fed via a gasometer on the carefully stirred suspension. After about 40 minutes, the saturation point was reached. The hydrogen consumption was about 620 cc at 25° C. In the course of 10 minutes, a solution of 1.76 g of Na$_2$SO$_3$ in 50 cc of water was then added dropwise, and stirring was continued for 60 minutes. The catalyst was separated by filtration from the liquid and washed with distilled water. It was used with a water content of about 50 percent.

We claim:

1. In a process for the preparation of 2,2'-dichlorohydrazobenzene by catalytic hydrogenation of o-nitrochlorobenzene in aqueous alkali metal hydroxide solution with addition of an aromatic non-watermiscible solvent at an elevated temperature and under pressure with a rare-metal catalyst and a polycyclic quinone co-catalyst the improvement comprising an anthraquinone as the co-catalyst.

2. A process as claimed in claim 1, wherein the alkali metal hydroxide solution is a sodium or potassium hydroxide solution.

3. A process as claimed in claims 1 or 2, wherein the alkali metal hydroxide solution has a concentration of 10 to 25% by weight.

4. A process as claimed in claim 1, wherein the aromatic non-watermiscible solvent is a hydrocarbon.

5. A process as claimed in claim 4, wherein the solvent is benzene, a lower-alkyl benzene or a mixture of such solvents.

6. A process as claimed in claim 4, wherein the solvent is toluene, a xylene, ethylbenzene or a mixture of two or more of such solvents.

7. A process as claimed in claim 1, wherein the temperature is 50° to 80° C.

8. A process as claimed in claim 1, wherein the temperature is 55° to 60° C.

9. A process as claimed in claim 1, wherein the hydrogenation is performed with a hydrogen over-pressure of 1 to 10 bars.

10. A process as claimed in claim 9, wherein the overpressure is 1 to 6 bars.

11. A process as claimed in claim 9 and 10, wherein the pressure rises within said limits during the hydrogenation.

12. A process as claimed in claim 1, wherein the catalyst is a palladium or platinum catalyst.

13. A process as claimed in claim 12, wherein the catalyst is a sulfided or sulfited platinum-on-carbon catalyst.

14. A process as claimed in claim 1, wherein the anthraquinone is a hydroxy-anthraquinone.

15. A process as claimed in claim 14, wherein the anthraquinone is β-hydroxy-anthraquinone or 2,6-dihydroxyanthraquinone.

16. A process as claimed in claim 1, wherein the aqueous alkali metal hydroxide solution is a sodium hydroxide solution having at the outset a concentration of 16 to 25% by weight.

17. A process as claimed in claim 1, wherein the ratio by weight of co-catalyst to o-chloro-nitrobenzene is 0.003 to 0.008:1.

18. A process as claimed in claim 1, wherein the ratio by weight of o-chloro-nitrobenzene to rare metal is 4000:1 to 1500:1.

19. A process as claimed in claim 18, wherein the ratio is 2500:1.

20. A process as claimed in claim 1, wherein the reaction mixture contains an emulsifier.

* * * * *